United States Patent [19]

Nakanishi et al.

[11] Patent Number: 4,850,991
[45] Date of Patent: Jul. 25, 1989

[54] ABSORBENT ARTICLE

[75] Inventors: Minoru Nakanishi; Akira Sakurai; Takatoshi Kobayashi, all of Utsunomiya; Zenbei Meiwa, Wakayama; Norihiro Abe, Utsunomiya, all of Japan

[73] Assignee: KAO Corporation, Tokyo, Japan

[21] Appl. No.: 94,908

[22] Filed: Sep. 10, 1987

[30] Foreign Application Priority Data

Sep. 17, 1986 [JP] Japan ................................ 61-218797
Nov. 5, 1986 [JP] Japan ................................ 61-263543

[51] Int. Cl.⁴ ............................................. A61F 13/16
[52] U.S. Cl. .................................. 604/387; 604/386; 604/369; 604/372; 604/391; 428/283; 428/317.7; 428/402; 428/407
[58] Field of Search ............ 604/369, 386, 387, 385.1, 604/372, 391; 428/313.5, 283, 913, 920, 402, 407, 317.3, 317.7

[56] References Cited

U.S. PATENT DOCUMENTS 3,643,662 2/1972 McGuire et al. .................... 604/387
3,881,490 5/1975 Whitehead et al. ............ 604/387 X
4,302,367 11/1981 Cordes et al. ...................... 260/17 R
4,576,610 3/1986 Donenfeld et al. ..................... 8/471

FOREIGN PATENT DOCUMENTS 2644032 4/1978 Fed. Rep. of Germany ...... 604/387
2374890 8/1978 France ................................ 604/387
2395141 2/1979 France ............................. 428/313.5

Primary Examiner—James C. Yeung
Assistant Examiner—Carl D. Price
Attorney, Agent, or Firm—Birch, Stewart, Kolasch & Birch

[57] ABSTRACT

An absorbent article comprises a liquid-permeable surface sheet, a liquid-impermeable leak-proof sheet and an absorbent layer disposed between the two sheets, said leak-proof sheet having on the outside surface a composite comprising a hydrophobic polymer having a glass transition temperature of zero degree centigrade or lower and foamed beads of a polymer. It is improved in the anti-slipping property, the leak-proof property and the permeability to moisture.

6 Claims, 2 Drawing Sheets

ABSORBENT ARTICLE

The present invention relates to an absorbent article such as sanitary napkin, a disposable diaper, a pad for incontinence, a pad for piles, or a pad for breast milk, and more specifically to an absorbent article having anti-slip properties and such an elasticity as to be capable of following the movement of the wearing portion of the body in at least part of a non-skin-contacting side of the article.

Figure 1:
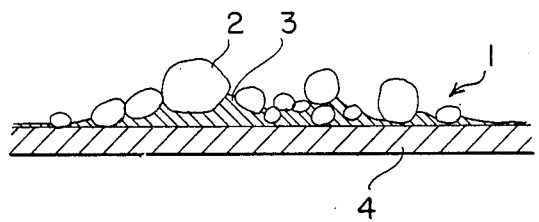
FIG. 1 is a crosssectional view of an example of a slip-preventing layer of an absorbent article according to the present invention.
Figure 2A:
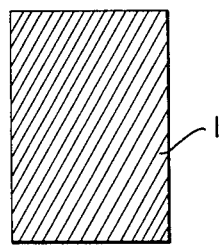
FIGS. 2(a)-2(f) are diagrams showing patterns of slip-preventing layers of absorbent articles according to the present invention in the non-skin-contacting side thereof.
Figure 2B:
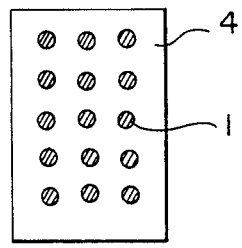
Figure 2C:
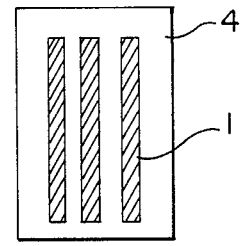
Figure 2D:
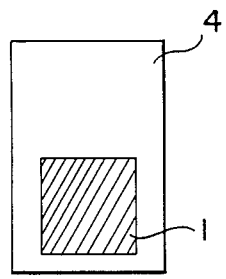
Figure 2E:
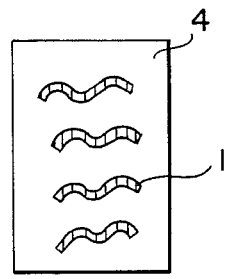
Figure 2F:
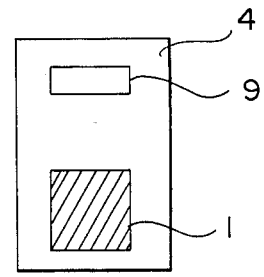
Figure 3A:
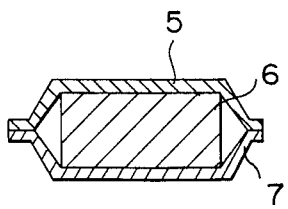
FIGS. 3(a)-3(e) show schematic crosssectional views of various embodiments of absorbent articles according to the present invention.
Figure 3B:
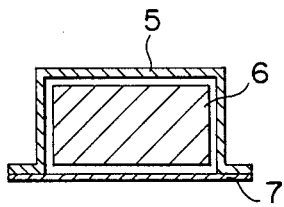
Figure 3C:
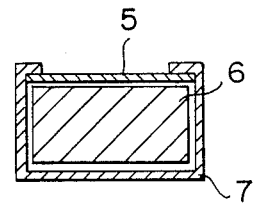
Figure 3D:
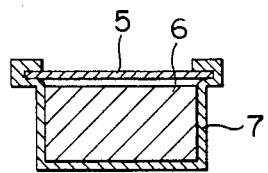
Figure 3E:
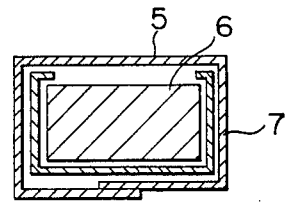

1: slip-preventing layer
2: foamed polymer beads
3: polymer having a glass transition temperature of 0° C. or lower
4: base layer
5: liquid-permeable surface material
6: absorbent layer
7: liquid-impermeably, leak-proof sheet
8: conventional absorbent article
9: double-side, pressure-sensitive adhesive tape
10: hot-melt, pressure-sensitive adhesive
11: movable female waist model
12: liquid dropping tube
13: test specimen

BACKGROUND OF THE INVENTION

A conventional absorbent article such as a sanitary napkin a pad for incontinence and a pad for piles is composed of an absorbent layer made of pulp or absorbent tissue, a leakproof sheet made of a waterproof paper or a so-called polymer-laminated waterproof paper having a polyethylene film laminated thereon for the purpose of preventing leakage, and a surface material covering the surface and the outer sides of the absorbent article.

The performance characteristics required of such an absorbent article are high absorption rate and high absorption retentivity. In order to attain these purposes, studies on surface materials and attempts to use the super absorbent polymer and another prior absorbent have recently been made. The inventors of the present invention has also expanded the above-mentioned idea and already proposed an absorbent material (Japanese Patent Laid-Open No. 55,260/1978) and an absorbent article (Japanese Patent Laid-Open No. 107,191/1979).

No matter how the performance of the absorbent layer may be improved, the performance becomes insignificant when shifts from a normal position such as a slip occurs in connection with the fit and movement in the crotch during use. Slip-preventing tapes have been proposed for the purpose of preventing shifts such as slip. For example, a sanitary napkin as a representative example of these absorbent articles will now be described. A slip-preventing tape was used in the sanitary napkin for the first time more than 10 years ago, and has been used up to now.

In an aspect of a material, a double-side pressure-sensitive adhesive tape and a hot-melt, pressure-sensitive adhesive have been used. With respect to shape, the former tape having a length of about 10 to 15 mm and a width of about 40 to 50 mm and applied to the napkin, and the latter adhesive having a length of 160 to 190 mm and a width of 3 to 5 mm and applied on the napkin, each having a release paper covering its surface, have been mainly provided.

However, it is difficult to determine the normal position with such a conventional slip-preventing tape when an article is put on for use, thus spoiling the fit to thereby cause a feeling of physical disorder. Since the front portion and the buttock side portion of the crotch are fundamentally different in movement during walking or exercise, slip or shift of a sanitary napkin itself occurs, providing an insufficient effect and often causing leakage of menstrual blood in absorption. This essentially spoils the performance of an absorbent article and, needless to say, results in mental uneasiness to a user.

Figure 4A:
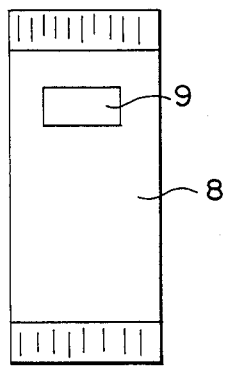
FIGS. 4(a)-4(c) are diagrams showing various examples of slip-preventing tapes of conventional absorbent articles provided on the non-skin-contacting side thereof.
Figure 4B:
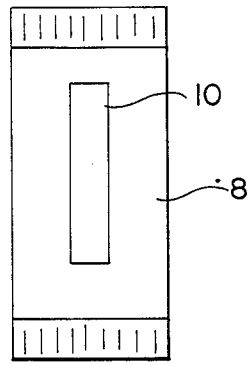
Figure 4C:
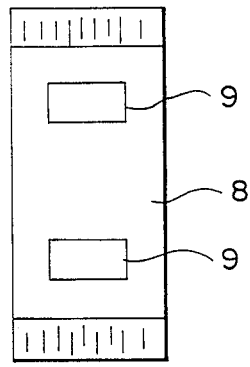

The problems of the slip-preventing tapes of conventional absorbent articles will now be described in detail with reference to the attached drawings. FIG. 4 shows various forms of slip-preventing tapes provided on the unused side (non-skin-contacting side) of the conventional absorbent article.

FIG. 4 (a) is a very common form, in which a double-side, pressure-sensitive adhesive tape 9 is provided in the lateral direction on a front portion of the absorbent article 8. Most of absorbent articles put on the market are of this type called a lateral single tape type. This type involves a comparatively no problem in ease of putting on, but provides a disadvantageous slip-preventing effect, attainment of which is the original purpose. Particularly the effect of preventing lateral slippage on the buttock side (the side having no slip-preventing tape) is insufficient.

On the other hand, FIG. 4 (b) is a case where a hot-melt adhesive is mainly used, namely a case where a hot-melt, pressure-sensitive adhesive 10 is extendedly provided in the longitudinal direction, and is called a longitudinal tape type. This type is thought to be improved in prevention of lateral slip as compared with the above-mentioned type, but such an effect cannot be obtained in reality. On the contrary, slip occurs and a feeling of physical disorder is felt in most cases. This is believed to be because the slip-preventing tape is folded in the central portion thereof in the crotch when the article is put on and a peculiar form is formed and set in the lateral direction. For this reason, the effective area of adhesion to shorts is extremely reduced, thus providing the above-mentioned disadvantages.

FIG. 4 (c) is a form which is believed to be proposed mainly for the purpose of improvement in prevention of the lateral slip. Double-side pressure-sensitive adhesive tapes 9 are provided in the lateral direction in two places in the front and rear portions of the absorbent article 8. This lateral double tape type fundamentally has the same demerits as those of the above-mentioned longitudinal tape type. Specifically, the type adheres to shorts when an article is put on, while at the same time the form in the longitudinal direction is set, thus providing a difference in the form from that in the state of usual use. It is difficult to put on an article with consideration given to that point, and even if possible, it is very troublesome to try it.

There have been proposed slip-preventing materials having a portion where a fiber such as nylon or rayon is bristled (Japanese Utility Model Laid-Open Nos. 44,097/1975, 44,098/1975 and 44,099/1975). However, these materials are difficult to set in a regular position when put on, and they are set in a state different from a complicated form of the crotch, thus causing a side leakage in walking or exercise.

There have been proposed methods using a structure having a contact surface of a relatively high friction coefficient, such as a foamed structure of foamed urethane or the like or a bristled structure of a flocked cloth or the like, as the non-self-adhesive slip-preventing material (Japanese Utility Model Laid-Open Nos. 46,319/1983, 105,318/1983, and 33,412/1984). However, the anti-slip effect obtained by a rough surface material such as a foamed structure is not so large that no sufficient slip-preventing effect can be expected in the actual us of an article only with such a structure. Thus, there have been proposed methods of combined use of the structure with a pressure-sensitive adhesive (Japanese Utility Model Laid-Open Nos. 88,421/1984 and 73,522/1985). In these methods, the effect of improving the fit with a contact surface is mainly aimed at by utilizing the rubber-like properties of the foamed material.

In the case of a flocked cloth, the slip-preventing effect can be sufficiently expected due to its higher friction coefficient than that of the foamed material, but the fit in the worn portion is poor because the cloth has no elongation. Further, the rate of bristling step cannot follow the napkin-producing rate which is now adopted, thus presenting a problem of a reduced processing rate.

In both cases as mentioned above, since an adhesive is needed for integration of the above-mentioned structure with a napkin or the like, the method cannot be said to be preferably from the viewpoint of the processing and the cost.

There also has been proposed a method of forming a non-slip foamed thin layer as a partition pattern from a foaming ink, which is usually used for preventing piles of goods such as corrugated boxes from falling (Japanese Utility Model Publication Nos. 31,227/1984 and 17,294/1984). Since the foaming ink is used mainly for the purpose of attaining uniformity and wear resistance of the foamed layer, however, a foaming polymer is not protruded from a binder resin layer and the binder resin is hard (glass transition temperature $Tg > 0°$ C.), so that the anchorage of the ink to the material in contact with it is poor, and no sufficient slip resistance is provided due to insufficient relaxation of the slip stress.

DESCRIPTION OF THE INVENTION

As a result of intensive investigations with a view to solving the problems of conventional absorbent articles, the inventors of the present invention have completed the present invention.

An object of the present invention is to provide an absorbent article having an anti-slip material which facilitates the location of the wearing position and exhibits an effective slip resistance against various movements of the crotch in the use of the absorbent article.

The present invention has been made for the purpose of attaining the above-mentioned object and providing an effective absorbent article to the user. Specifically, the invention relates to an absorbent article having an anti-slip material, which does not need a highly sophisticated technique in the production, which facilitates the location of the wearing position in the use thereof, and which exhibits an effective slip resistance against various movements of the crotch during the use thereof.

An absorbent article of the invention comprises a liquid-permeable surface sheet, a liquid-impermeable leak-proof sheet and an absorbent layer disposed between the two sheets, said leak-proof sheet having on the outside surface a composite comprising a hydrophobic polymer having a glass transition temperature of zero degrees centigrade or lower and foamed beads of a polymer.

The layer of the composite is placed on the back surface not to contact with the skin of a user of the absorbent article of the invention and serves to prevent the resulting article from slipping and improves the leak-proof properties and permeabilities to moisture.

Accordingly the composite may be combined with the back sheet or leak-proof sheet in any way as far as the above shown advantages can be attained. For example, the leak-proof sheet may have on a part or all of the outside surface thereof the composite to form a slip-preventing layer. Another way the composite is supported is on a sheet of fibrous material base. Alternatively the leak-proof sheet comprises said composite and a sheet of fibrous material base.

DETAILED DESCRIPTION OF THE PREFERRED EMBODIMENT

The invention article will be explained in detail in reference to a preferable embodiment.

Specifically, the present invention provides an absorbent article characterized by having a slip-preventing layer composed of a polymer having a glass transition temperature of 0° C. or lower and foamed polymer beads and provided in at least part of the lowermost layer constituting a non-skin-contacting side of the absorbent article.

The absorbent article of the present invention is obtained by printing or coating a mixture of a polymer having a glass transition temperature of 0° C. or lower and thermally expansible polymer beads on at least part of the lowermost layer of the absorbent article constituting a non-skin-contacting side, and heating them to foam the foaming polymer beads.

Various polymers are usable as the polymer having a glass transition temperature of 0° C. or lower. Specific examples of them include polymers of alkyl (meth)acrylates such as methyl (meth)acrylate, butyl (meth)acrylate, and 2-ethylhexyl (meth)acrylate; acrylic resins containing a plurality of kinds of alkyl (meth)acrylate units as the main components; synthetic rubbers such as styrene-butadiene rubber (S.B.R.), carboxy-modified S.B.R., nitrile-butadiene rubber (N.B.R.), and butadiene rubber (B.R.); polyurethane resins; polyvinyl chloride resins; and polyvinylidene chloride resins. These resins may be used alone or as a mixture. The resin may be used in the form of an emulsion containing the resin dispersed in water or a solution containing the resin dissolved in an organic solvent. The emulsifier or the organic solvent to be used for obtaining the above-mentioned form may be a commonly known solvent. The method for obtaining the above-mentioned form may also be a known one. The resin may contain a crosslinking agent, if necessary.

In the present invention, a plasticizer or the like may be added to the above-mentioned polymer if necessary in order to lower the glass transition temperature to 0° C. or lower.

The heat foaming polymer beads to be used in obtaining the absorbent article of the present invention may be ones having shell walls made of a thermoplastic copolymer resin and a butane gas or the like encapsulated therein (e.g., Matsumoto Microspheres, which is a trade name of a product manufactured by Matsumoto Yushi Seiyaku K.K.).

The weight ratio (in terms of solids content) of the polymer having a glass transition temperature of 0° C. or lower to the heat foaming polymer beads is 95:5 to 40:60, preferably 90:10 to 50:50. When this ratio exceeds 95:5, the slip resistance is insufficient. When it is less than 40:60, the falling off of the heat foaming polymer beads is unfavorably observed after foaming.

A mixture of the polymer having a glass transition temperature of 0° C. or lower and the heat foaming polymer beads can be prepared by a known method. A thickener may be added to the mixture in order to improve the stability, printability, or applicability of the mixture.

The weight of the mixture of the polymer having a glass transition temperature of 0° C. or lower and the heat foaming polymer beads which is applied to a non-skin-contacting side is 0.1 to 30 g/m$^2$, preferably 0.5 to 20 g/m$^2$, in terms of solids content after foaming.

In general, as the amount of application is increased, the leak-preventing properties and anti-slip properties tend to increase, while the moisture-permeability tends to increase as the amount of application is decreased.

A composite comprising a mixture of a hydrophobic polymer emulsion and a heat-foaming polymer beads applied onto the sheet-form fibrous base is dried and foamed by a known method using hot air, infrared rays, electromagnetic radiation, or steam.

As shown in FIG. 1, the composite 1 to use as the leakproof sheet according to the present invention comprises foamed polymer beads (microcapsular portions) 2 having a complicated uneven shape protruded from the surface, and a hydrophogic polymer portion 3 having a glass transition temperature of 0° C. or lower and connecting the beads to a sheet-form fibrous base 4.

The reason why the leakproof sheet according to the present invention has a moisture permeability, leak-preventing properties and anti-slip properties is not necessarily elucidated. As for the moisture permeability and leak-preventing properties, however, it is believed that the fibers of the sheet-form fibrous base pierce the hydrophobic polymer in many portions so that microscopic phase separation is caused in the interfaces between the fibers and the hydrophobic polymer to form micropores, whereby favorable moisture permeability and leak-preventing properties are exhibited. As for anti-slip properties, it is believed that, since the foamed microcapsular portions having a complicated uneven structure are usually more flexible than a base cloth, the anchorage thereof to the base cloth is good and that, since the microcapsular portions are bonded with the flexible polymer, the slippage stress put on the microcapsular portions is absorbed and relaxed by the rubber elasticity to exhibit a high slip resistance.

Utilizable methods of application of the mixture include known printing methods such as screen printing, gravure printing and flexographic printing; and known coating methods such as spray coating and roll coating.

In the present invention, the material of the lowermost layer constituting a non-skin-contacting side may be, for example, a water-proof paper or non-woven fabric having a polyethylene film laminated thereon, or a surface material of a non-woven fabric where the whole structure is covered with the surface material. Needless to say, the material in the present invention is not limited to these materials.

As shown in FIG. 1, the slip-preventing layer 1 according to the present invention comprises foamed polymer beads (microcapsule portions) 2 having a complicated uneven shape protruded from the surface, and a polymer having a glass transition temperature of 0° C. or lower (rubber elastic resin portion) 3 connecting the beads to a base layer 4. A high slip resistance is generated by the balance of rigidity or flexibility of the base layer 4 in contact with the slip-preventing layer 1, the microcapsule portions 2 and the rubber elastic resin portion 3. Specifically, since the foamed microcapsule portions forming an uneven surface are usually more flexible than a base cloth such as shorts, the anchorage thereof to the base cloth is good. Further, since the microcapsule portions are bonded with the flexible polymer, the slippage stress put on the micrcocapsule portions is absorbed and relaxed by the rubber elasticity to exhibit a high slip-resistance.

The slip-preventing layer 1 must not always be provided on the whole surface of the base layer 4 (non-skin-containing side). Various patterns of a slip-preventing layer can be provided as shown in FIGS. 2 (a) to (f). In order to secure a sufficient slip-preventing effect, the slip-preventing layer is preferably provided on 10% or more of the non-skin-contacting side.

If necessary, a combined use of the slip-preventing layer with a double-side, pressure-sensitive adhesive tape or a hot-melt, pressure-sensitive adhesive is possible as shown in FIG. 2 (f).

FIG. 3 shows embodiments of the absorbent article of the present invention. FIGS. 3 (A) to (E) are various forms composed of a liquid-permeable surface material 5, an absorbent layer 6, and a liquid-impermeable leakproof sheet. Needless to say, the present invention is not limited to these forms.

Since the absorbent article of the present invention has an anti-slip or slip-preventing layer having a high slip resistance and provided on the lowermost layer thereof (non-skin-contacting side), the slip-preventing layer effectively contacts with shorts or the like while wearing to effectively prevent the slip because of the high frictional resistance of the slip-preventing layer. Further, the slip-preventing action is different from that of the conventional methods in that it is not an adhesive. Thus, even if the absorbent article unfortunately is not put on in the original, normal form, it can be fitted to the crotch form and the above-mentioned slip-preventing effect is exhibited since the absorbent article of the present invention is free from such demerits of the conventional ones that the adhesive is bonded with each other so that difficulty is encountered in returning to the normal form.

Since a very high slip resistance is exhibited with a small amount of coating, the hand of the base layer is not spoiled, and the cost is very advantageous.

In the absorbent article of the present invention, the slip resistance can be varied by varying the combination of a polymer having a glass transition temperature (Tg) of 0° C. or lower and heat foaming polymer beads, and the slip resistance can be arbitrarily set according to need.

Another preferably embodiment of the invention will be explained below.

The present invention has been made with a view to attaining the above-mentioned objects and providing a beneficial absorbent article to users. Specifically, the present invention relates to an absorbent article which does not require so advanced a technique in the production thereof, and which has effective moisture-permeability and anti-slip properties.

Specifically, the present invention provides an absorbent article comprising a liquid-permeable surface sheet, a liquid-impermeable leakproof sheet, and an absorbent layer disposed between the two sheets, characterized in that the leakproof sheet is a composite comprising a sheet-form fibrous base, a hydrophobic polymer having a glass transition temperature of 0° C. or lower and foamed polymer beads, that at least one side of the sheet-form fibrous base is covered with the hydrophobic polymer, and that the foamed polymer beads are fixed onto the sheet-form fibrous base via the hydrophobic polymer.

Embodiments of the present invention will now be described with reference to the attached drawings, but, needless to say, they should not be construed as limiting the scope of the invention.

FIGS. 7(a) to (d) are crosssectional views of sanitary napkins showing various examples of the absorbent article of the present invention. Briefly speaking, the absorbent article of the present invention is constituted of a surface sheet 7, an absorbent layer 6 and a leakproof sheet 5. The present invention is characterized by the leakproof sheet 5. The leakproof sheet according to the present invention is obtained by printing or coating at least one side of a sheet-form fibrous base with a mixture of a hydrophobic polymer having a glass transition temperature of 0° C. or lower and a heat-foaming polymer, drying the same in such a state that the mixture can be in filtered into the sheet-form fibrous base, and heating them to foam the heat-foaming polymer.

A wet membrane forming process is known as a process for preparing a moisture-permeable membrane. Specifically, according to this technique, a solution of a hydrophobic polymer is treated with a liquid which is a non-solvent for the hydrophobic polymer and is freely miscible with the solvent of the hydrophobic polymer solution, to thereby coagulate the polymer, while forming micropores in the resulting membrane. However, it is very difficult to form uniform pores according to this process.

Further, there is known a technique for obtaining a moisture-permeable membrane which comprises preliminarily adding a low molecular weight substance; an inorganic salt, or the like to a hydrophobic polymer solution, forming a membrane from them, and dissolving away the additive with a solvent which is a non-solvent for the polymer and can dissolve the additive (see, e.g., Japanese Patent Laid-Open No. 19,704/1973). In this technique, the amount of the additive must be increased to impart a moisture-permeability to the resulting membrane, and hence the water resistance is disadvantageously decreased. When the low molecular weight substance, the inorganic salt, or the like is uniformly mixed with the hydrophobic polymer solution and a membrane is formed therefrom, an extreme difficulty is encountered in completely dissolving out the above-mentioned additive. Thus, a uniform moisture-permeable membrane is hardly obtained.

Since the conventional processes for preparing a moisture-permeable membrane involve the above-mentioned defects, strict control of production conditions and complicated steps are required and the productivity is poor. Thus, the use of membranes formed by the conventional processes as the leakproof sheet of a bodily fluid-absorbent article is quite unsatisfactory.

The leakproof sheet according to the present invention is prepared by printing or coating at least one side of a sheet-form fibrous base with a mixture of a hydrophobic polymer having a glass transition temperature of 0° C. or lower and a heat-foaming polymer, drying the same in such a state that the mixture can be infiltrated into the sheet-form fibrous base, and heating them to foam the heat-foaming polymer. It is a moisture-permeable membrane having such a structure that the hydrophobic polymer infiltrates into the sheet-form fibrous base to cover the spaces between the fibers of the fibrous base with thin films of the hydrophobic polymer. This moisture-permeable membrane is produced by simple steps of application and drying unlike the conventional processes, whereby the productivity is good. Thus, the membrane can be satisfactorily used in an absorbent article.

Any fibrous material as generally used in paper, nonwoven fabric or the like may be used in the sheet-form fibrous base to be used in the present invention. Examples of such a fibrous material include cellulosic fibers such as wood pulp, rayon, and cotton; and polyethylene, polypropylene, polyester, Vinylon, polyethylene-polypropylene conjugate, polyethylene-polyester conjugate, ethylene-vinyl acetate copolymer, and ethylene-ethyl acrylate copolymer fibers. Any sheet formed from such a fibrous material by a dry process or a wet process can be used in so far as it has such spaces between fibers as will allow a vapor or the like to pass therethrough. Needless to say, the present invention is not limited to the above-mentioned materials.

The sizing treatment may be conducted if necessary in consideration of the water resistance of the sheet.

The leak-preventing properties of an absorbent article such as a sanitary napkin, a disposable diaper, or the like are satisfactory when the hydraulic pressure resistance (JIS L-1092) of the leakproof sheet is 50 cm or more (in the case of wearing it for a long time, the preferable hydraulic pressure resistance is 100 cm or more). When the moisture permeability (JIS Z-0208) is 600 g/m$^2$·24 hr or more, the effect of preventing "stuffiness" and "rash" is exhibited.

The leakproof sheet according to the present invention is produced under such conditions as will satisfy the above-mentioned requisites, and has a bodily fluid impermeability and a moisture permeability.

Since the absorbent article of the present invention is constituted as described above and has a bodily fluid impermeability, a moisture permeability, and anti-slip properties, it does not cause "stuffiness" in its use, facilitates putting the same on, well fits the complicated form of the crotch in putting the same on, and exhibits an excellent effect of preventing slip.

EXAMPLES

The following Examples will illustrate the present invention in more detail, but should not be construed as limiting the scope of the invention.

The slip resistance was measured by the following procedure.

SLIP RESISTANCE

Figure 5:
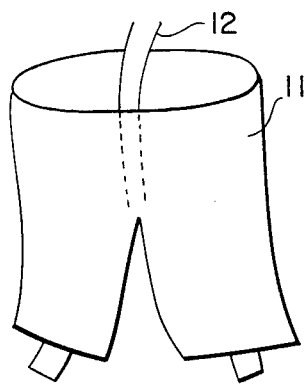
FIG. 5 is a perspective view of a movable female waist model.
Figure 6:
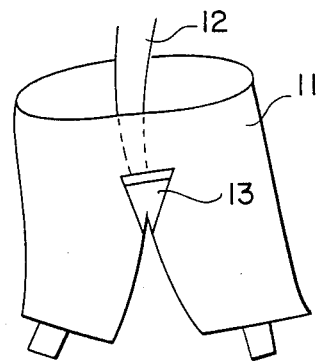
FIG. 6 is a perspective view showing the state of a test specimen worn on the movable female waist model.

A test specimen 13 was put on a movable female waist model 11 as shown in FIG. 5 in such a way as shown in FIG. 6. After shorts were put on, the model was set in walking movement at a rate of 50 m/min for 10 min. The position of the test specimen 13 and that when it was put on were measured, and the distance therebetween was regarded as the slip resistance in a dry state.

5 g of artificial blood was absorbed into a test specimen 13 through a dropping tube 12 in the state of wearing the specimen. The model was set in walking movement at the same rate for 10 min. The slip was examined in the same manner as described above. The distance as mentioned above was regarded as the slip resistance in an absorbed state.

The measurement was made with 10 test specimens, and an average value thereof was calculated.

The constitutions of the test specimens were of two kinds as shown in FIG. 3 (A) and FIG. 3 (B). In each case, 2.0 g of a fluff pulp, 1.2 g of an absorbent paper and 0.3 g of a super absorbent polymer were used in an absorbent layer 6. 20 g/m² of a polyolefin type material (polyethylene-polypropylene conjugate fiber/polyester: 30/70 by weight) was used as the surface material 5.

polypropylene conjugate fiber and a polyester and then laminated thereon with polyethylene, having a basis weight of 20 g/m2, by using a gravure press, a gravure roll being a solid plate having a lattice of 40 mesh, being available from Hirano Kinzoku K.K.

The mixture was also applied on a polyethylene-laminated, non-woven fabric and a polyethylene-laminated, water-proof paper in the same manner as that described above. After printing, the printed materials were preliminarily dried in a circulating hot air drier at 60° C. and subjected to a heat foaming treatment in a circulating hot air drier at 110° C. to provide a slip-preventing layer on a base layer. The base layer having a slip-preventing layer provided in such a way on the non-skin-contacting side was constituted as shown in FIG. 3 to afford an article according to the present invention.

EXAMPLE 2

Articles according to the present invention were obtained by using Matsumoto Microsphere F-30 and by varying the substrate, the kind of polymer having a glass transition temperature of 0° C. or lower, the amount of coating, the pattern of coating, the manner of constitution, etc. as shown in Table 1 in substantially the same manner as in Example 1. The slip resistances of these articles are shown in Table 1.

An article having no slip-preventing layer and an article having a double-side, pressure-sensitive adhesive tape as shown in FIG. 4 (c) were examined with respect to the slip resistance as comparative articles. The results are shown in Table 1.

It is apparent from Table 1 that the articles according to the present invention have a high slip resistance.

TABLE 1

| Base layer | Kind of polymer | Tg (°C.) | Amount of coating (g/m²) | Coating pattern | Constitution | Slip (mm) In dry state | Slip (mm) In absorbed state | Remarks |
| --- | --- | --- | --- | --- | --- | --- | --- | --- |
| non-woven fabric polyethylene laminate | polybutyl acrylate | −49 | 4 | FIG. 2 (a) | FIG. 3 (A) | 1 | 1 | |
| " | poly-2-ethylhexyl acrylate | −63 | 4 | FIG. 2 (b) | FIG. 3 (A) | ~0 | 1 | |
| " | AE-516*1 | −48 | 2 | FIG. 2 (c) | FIG. 3 (B) | 2 | 3 | present |
| " | styrene-butadiene copolymer | −20 | 2 | FIG. 2 (e) | FIG. 3 (B) | 1 | 2 | invention |
| water-proof paper/ polyethylene | AE-516 | −48 | 2 | FIG. 2 (a) | FIG. 3 (B) | ~0 | 1 | |
| non-woven fabric/ polyethylene laminate | — | | 0 | — | FIG. 3 (A) | 60 | 63 | comparative |
| non-woven fabric/ polyethylene laminate | Double-side pressure-sensitive adhesive tape was provided as in FIG. 4 (c). | | | | FIG. 3 (A) | 7 | 9 | comparative |

Note
*1Self-crosslinkable acrylic emulsion manufactured by Japan Synthetic Rubber Co., Ltd.

EXAMPLE 1

1,780 g of self-crosslinkable acryl emulsion AE-516 (manufactured by Japan Synthetic Rubber Co., Ltd., solids content: 45%, glass transition temperature: −48° C.), 280 g of Matsumoto Microsphere F-30, 16.5 g of sodium carboxymethylcellulose as a thickener, and 1,270 g of water were mixed in a homomixer for 1 hour to obtain a mixture.

The mixture was applied in an amount of 2 g/m² as solids on a non-woven fabric made of a polyethylene- The moisture permeability and the hydraulic pressure resistance were measured in accordance with JIS Z-0208 and JIS L-1092, respectively. The slip resistance was measured in the following manner.

Figure 7A:
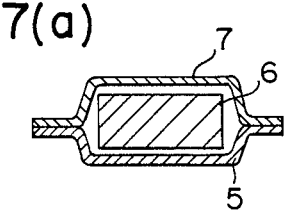
FIGS. 7(a)-7(d) show crosssectional views of various embodiments of absorbent articles according to the present invention.
Figure 7B:
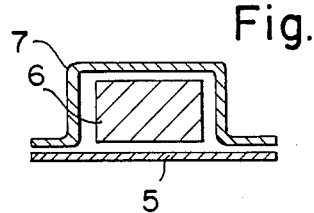
Figure 7C:
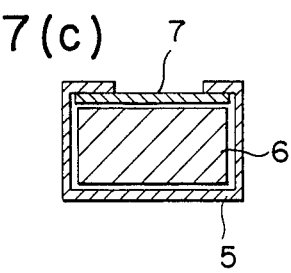
Figure 7D:
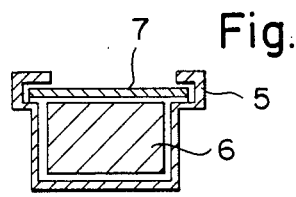

Test samples were prepared as shown in FIG. 7(b). The absorbent layer therein was produced in the same manner as shown in Example 1.

EXAMPLE 3

1780 g of self-crosslinked acrylic emulsion AE-516 (manufactured by Japan Synthetic Rubber Co., Ltd., solids content: 45%, glass transition temperature: −48° C.) was mixed with 280 g of Matsumoto Microsphere F-30, 16.5 g of sodium carboxymethylcellulose as a thickener and 1270 g of water in a homomixer for one hour to obtain a mixture.

The mixture was applied in an amount of 8 g/m$^2$ as solids onto a paper subjected to a wax size treatment (pulp: 100%, basis weight: 25 g/m$^2$) by using a gravure press (manufactured by Hirano Kinzoku K.K., gravure roll: solid plate, lattice: 40-mesh). After printing, the printed material was preliminarily dried in a circulating hot air drier at 60° C. and heat-treated in a circulating hot air drier at 110° C. to obtain a moisture-permeable anti-slip sheet. This sheet was used in a constitution as shown in FIG. 7(b) to obtain an article according to the present invention.

EXAMPLE 4

Articles according to the present invention were obtained by using Matsumoto Microsphere F-30 and by varying the kinds of sheet-form fibrous base and hydrophobic polymer having a glass transition temperature of 0° C. or lower as shown in Table 2 in substantially the same manner as that of Example 3.

The absorbent articles obtained in Example 3 and 4 were examined with respect to moisture permeability, leak-preventing properties, and slip resistance. The results are shown in Table 2.

Comparative absorbent articles respectively using a polymer-laminated paper and a polyethylene sheet as used in absorbent articles such as a sanitary napkin and a disposable diaper were examined with respect to moisture permeability, leak-preventing properties, and slip resistance. The results are shown in Table 2.

It is apparent from Table 2 that the articles according to the present invention have high moisture permeability, leak-preventing properties, and slip resistance.

What is claimed is:

1. An absorbent article which comprises a liquid permeable surface sheet, a liquid-impermeable leak-proof sheet and an absorbent layer disposed between said liquid permeable surface sheet and a first surface of said liquid impermeable leak-proof sheet, said leak-proof sheet having a second surface, said leak-proof sheet being a fibrous material base layer and a composite, said composite being disposed on said second surface and being made of a hydrophobic polymer having a glass transition temperature of 0° C. or less and foamed polymer beads, wherein the weight ratio in terms of solids content of said hydrophobic polymer to said foamed polymer beads range between 95 to 5 and 40 to 60, and wherein said beads are fixed on said fibrous material base by said hydrophobic polymer.

2. The absorbent article according to claim 1 wherein the weight in terms of solids content of the mixture of said hydrophobic polymer and said foamed polymer beads is 0.1 to 30 g/m$^2$.

3. The absorbent article according to claim 2 wherein said weight is 0.5 to 20 g/m$^2$.

4. The absorbent article according to claim 1, wherein said foamed beads have shell walls made of a thermoplastic copolymer resin with a gas encapsulated therein.

5. The absorbent article according to claim 1, wherein said weight ratio in terms of solids content of said hydrophobic polymer to said foamed polymer beads is 90:10 to 50:50.

6. An absorbent article as claimed in claim 1, in which said leak-proof sheet has on a part or all of the outside surface thereof the composite to form a slip-preventing layer.

* * * * *

TABLE 2

| | Sheet-form fibrous base | Hydrophobic polymer (trade name) | Application method | Amount of application (g/m$^2$) | Moisture permeability (g/m$^2$ · 24 hr) | Hydraulic pressure resistance (cm) | Slip distance (mm) in dry state | Slip distance (mm) in absorbed state |
|---|---|---|---|---|---|---|---|---|
| Ex. 3 | paper treated with wax size (pulp: 100%) | AE-516[1] | gravure printing | 8 | 1450 | >200 | 1 | 1 |
| Ex. 4-1 | " | AE-516[1] | screen printing | 4 | 1820 | 108 | 2 | 3 |
| Ex. 4-2 | wet process non-woven fabric of autohesion type (rayon: 100%) | AE-812[2] | gravure printing | 8 | 820 | >200 | ~0 | 1 |
| Ex. 4-3 | dry process spun bonded fabric (PET: 100%) | 0696[3] | " | 20 | 1720 | >200 | 2 | 3 |
| Ex. 4-4 | " | Krehalon Latex LA-412[4] | screen printing | 20 | 1630 | 137 | 1 | 3 |
| Ex. 4-5 | wet process non-woven fabric (PET: 60%, EA: 40%) | AE-336[5] | " | 10 | 1820 | 62 | 2 | 3 |
| Comp. Article | polyethylene-laminated paper | | | 7 | | >200 | 60 | 63 |
| Comp. Article | polyethylene sheet | | | 10 | | >200 | 58 | 61 |

Note
[1] acrylic emulsion of self-crosslinked type, manufactured by Japan Synthetic Rubber Co., Ltd.
[2] acrylic emulsion of highly carboxy-modified type, manufactured by Japan Synthetic Rubber Co., Ltd.
[3] carboxy-modified styrene-butadiene copolymer, available from Japan Synthetic Rubber Co., Ltd.
[4] polyvinylidene chloride latex, manufactured by Kureha Chemical Industry Co., Ltd.
[5] acrylic emulsion of soap-free type, manufactured by Japan Synthetic Rubber Co., Ltd.